(12) United States Patent
Jackson

(10) Patent No.: US 7,651,502 B2
(45) Date of Patent: Jan. 26, 2010

(54) SPINAL FIXATION TOOL SET AND METHOD FOR ROD REDUCTION AND FASTENER INSERTION

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 849 days.

(21) Appl. No.: 10/950,377

(22) Filed: Sep. 24, 2004

(65) Prior Publication Data

US 2006/0074418 A1    Apr. 6, 2006

(51) Int. Cl.
*A61B 17/58* (2006.01)
*A61F 2/00* (2006.01)
(52) U.S. Cl. ........................................ 606/99
(58) Field of Classification Search ............... 606/86 A, 606/99, 104, 105, 246; 81/99, 101–105, 81/111–116
See application file for complete search history.

(56) References Cited

U.S. PATENT DOCUMENTS

| | | | |
|---|---|---|---|
| 854,956 A | 5/1907 | Martin | |
| 2,524,095 A * | 10/1950 | Williams | 81/453 |
| 2,669,896 A * | 2/1954 | Clough | 81/128 |
| 5,020,519 A | 6/1991 | Hayes et al. | |
| 5,092,866 A | 3/1992 | Breard et al. | |
| 5,282,862 A | 2/1994 | Baker et al. | |
| D346,217 S | 4/1994 | Sparker et al. | |
| 5,330,472 A | 7/1994 | Metz-Stavenhagen | |
| 5,360,431 A | 11/1994 | Puno et al. | |
| 5,409,489 A | 4/1995 | Sioufi | |
| 5,484,437 A | 1/1996 | Michelson | |
| 5,484,440 A | 1/1996 | Allard | |
| 5,647,873 A | 7/1997 | Errico et al. | |
| 5,720,751 A | 2/1998 | Jackson | |
| 5,782,830 A | 7/1998 | Farris | |
| 5,792,044 A | 8/1998 | Foley et al. | |
| 5,810,816 A | 9/1998 | Roussouly et al. | |
| 5,817,094 A | 10/1998 | Errico et al. | |

(Continued)

FOREIGN PATENT DOCUMENTS

EP    1190678    3/2002

(Continued)

OTHER PUBLICATIONS

Brochure of Spinal Concepts, *Pathfinder, Minimally Invasive Pedicle Fixation System*, Publication Date: May 2003.

(Continued)

*Primary Examiner*—Anu Ramana
(74) *Attorney, Agent, or Firm*—John C. McMahon

(57) ABSTRACT

A tool for implantation of a rod into a bone screw implanted in a human spine includes a guide member having a laterally opening channel disposed along an entire length thereof for side loading and receiving an implant fastener. A rod pushing member and a handle with a laterally opening channel are coaxial with the guide member, with the rod pushing member being rotatingly mateable to the guide member and the handle having a spring attachment mechanism for attaching the handle to the guide member. The guide member includes spring tabs for attachment to a bone screw, the tabs biased away from the bone screw. The rod pushing member includes a sleeve that extends substantially about the guide member, pressing the spring tabs toward the bone screw and into apertures on the bone screw arms. The rod pushing member sleeve also operatively functions as a rod pusher that abuts a rod as the sleeve is translated along the guide member and toward the bone screw. The handle lateral opening receives and supports a manipulation tool for inserting and installing an implant fastener for attaching the rod to the bone screw.

8 Claims, 8 Drawing Sheets

U.S. PATENT DOCUMENTS

| | | | |
|---|---|---|---|
| 5,891,145 | A | 4/1999 | Morrison et al. |
| 5,902,231 | A | 5/1999 | Foley et al. |
| 5,910,141 | A | 6/1999 | Morrison et al. |
| 6,063,088 | A | 5/2000 | Winslow |
| 6,183,472 | B1 | 2/2001 | Lutz |
| 6,235,028 | B1 | 5/2001 | Brumfield et al. |
| 6,248,107 | B1 | 6/2001 | Foley et al. |
| 6,251,112 | B1 | 6/2001 | Jackson |
| 6,277,122 | B1 | 8/2001 | McGahan et al. |
| 6,280,445 | B1 | 8/2001 | Morrison et al. |
| 6,309,391 | B1 | 10/2001 | Crandall et al. |
| 6,315,779 | B1 | 11/2001 | Morrison et al. |
| 6,331,179 | B1 | 12/2001 | Freid et al. |
| 6,440,133 | B1 | 8/2002 | Beale et al. |
| 6,443,956 | B1 | 9/2002 | Ray |
| 6,478,801 | B1 | 11/2002 | Ralph et al. |
| 6,511,484 | B2 | 1/2003 | Torode et al. |
| 6,520,962 | B1 | 2/2003 | Taylor et al. |
| 6,530,929 | B1 | 3/2003 | Justis et al. |
| 6,562,038 | B1 | 5/2003 | Morrison |
| 6,572,618 | B1 | 6/2003 | Morrison |
| 6,599,294 | B2 | 7/2003 | Fuss et al. |
| 6,635,060 | B2 | 10/2003 | Hanson et al. |
| 6,648,888 | B1 | 11/2003 | Shluzas |
| 6,660,006 | B2 | 12/2003 | Markworth et al. |
| 6,778,861 | B1 | 8/2004 | Liebrecht et al. |
| 6,790,208 | B2 | 9/2004 | Oribe et al. |
| 6,790,209 | B2 | 9/2004 | Beale et al. |
| 2001/0001119 | A1 | 5/2001 | Lombardo |
| 2002/0095153 | A1 | 7/2002 | Jones et al. |
| 2003/0225408 | A1 | 12/2003 | Nichols et al. |
| 2003/0236529 | A1 | 12/2003 | Shluzas et al. |
| 2005/0171542 | A1 | 8/2005 | Biedermann et al. |
| 2005/0182410 | A1 | 8/2005 | Jackson |
| 2005/0192580 | A1 | 9/2005 | Dalton |

FOREIGN PATENT DOCUMENTS

| | | |
|---|---|---|
| FR | 2729291 | 7/1996 |
| FR | 2796545 | 1/2001 |
| WO | WO2004/041100 | 5/2004 |

OTHER PUBLICATIONS

Brochure of Spinal Concepts, an Abbott Laboratories Company, *Pathfinder, Minimally Invasive Pedicle Fixation System*, Publication Date: Nov. 2003.

Brochure of Spinal Concepts, *InCompass, Thoracolumbar Fixation System*, Publication Date: Oct. 2003.

Brochure of Spinal Concepts, Surgical Technique, *InCompass, Thoracolumbar Fixation System*, Publication Date: Oct. 2003.

Brochure of SpineLine, Current Concepts, *Minimally Invasive Posterior Spinal Decompression and Fusion Procedures*, Publication Date: Sep./Oct. 2003.

Brochure of Sofamor Danek the Spine Specialist, TSRH, *Pedicle Screw Spinal System*, Publication Date: Jan. 23, 1995.

\* cited by examiner

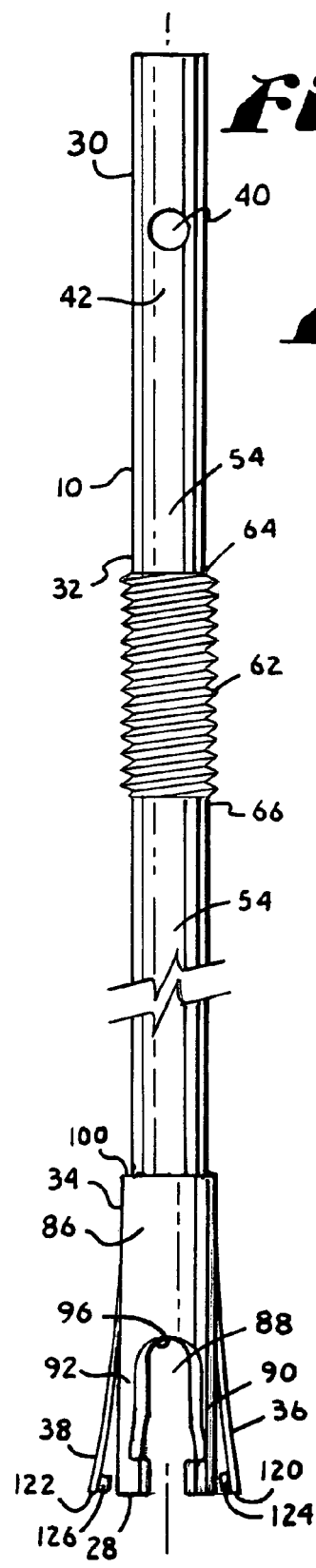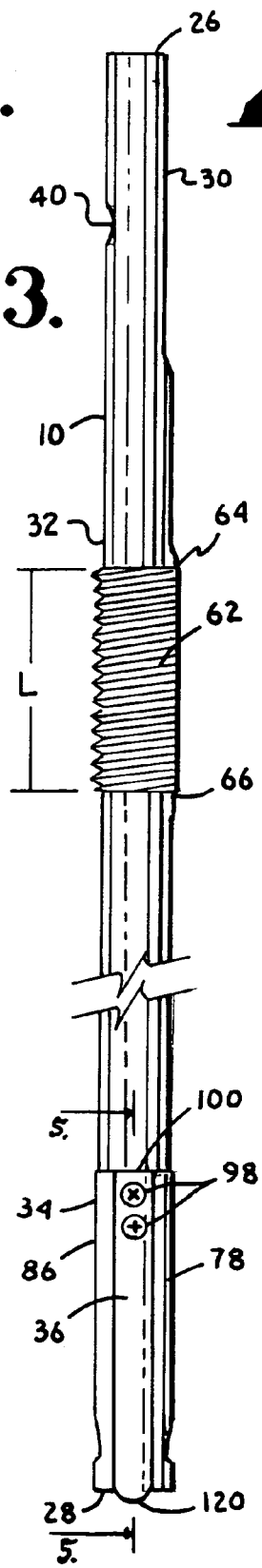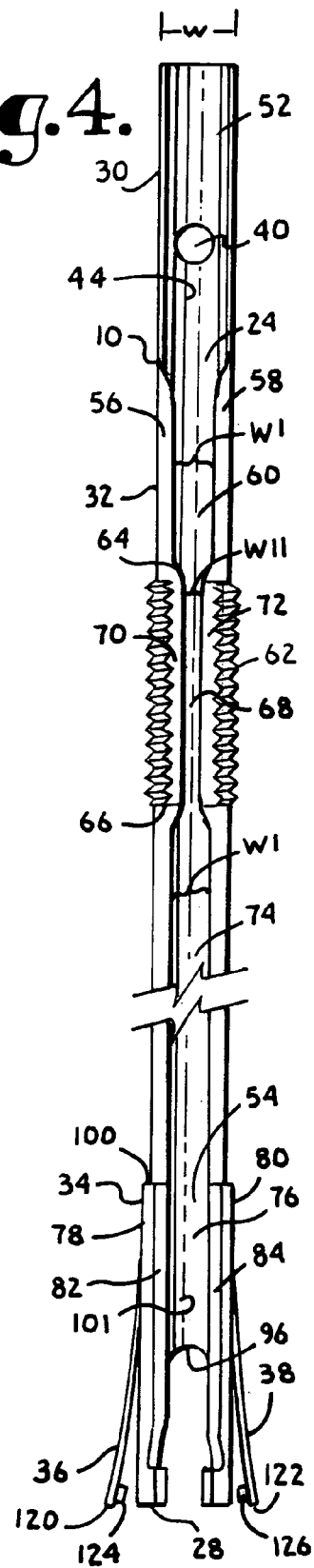

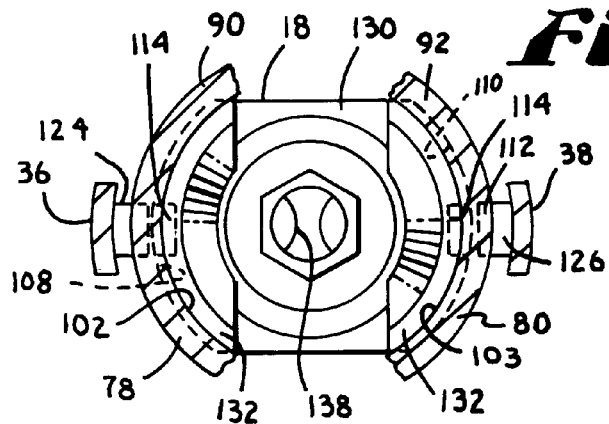
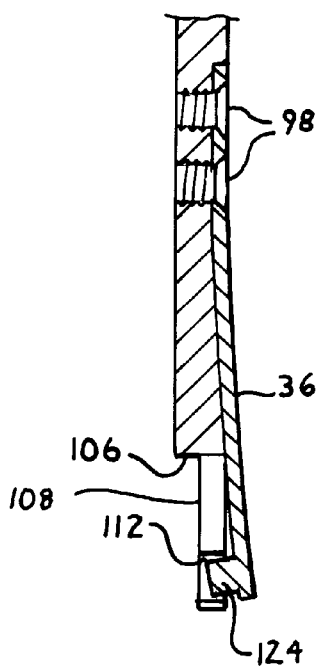
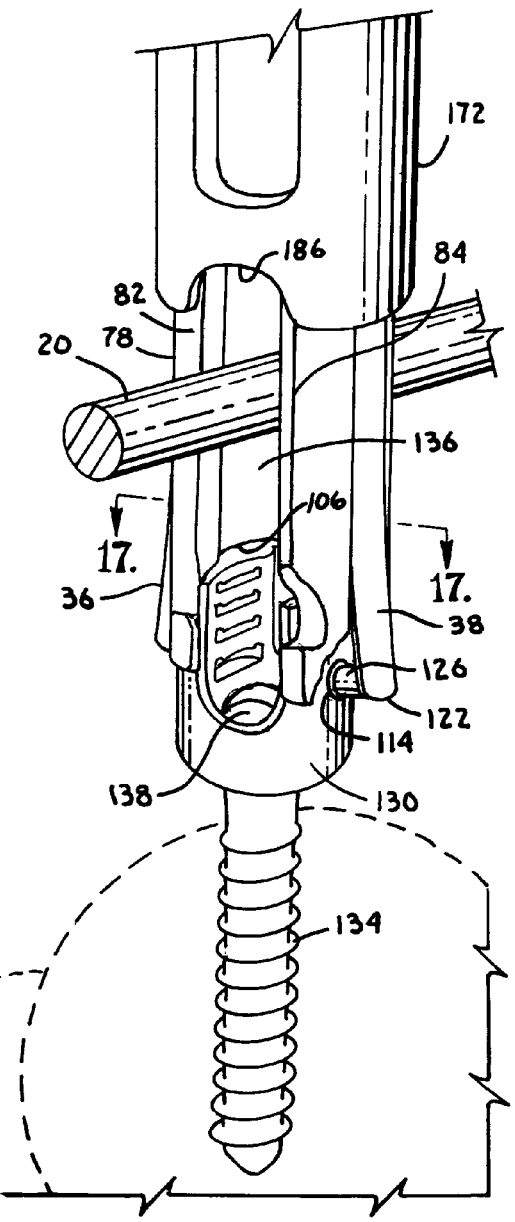

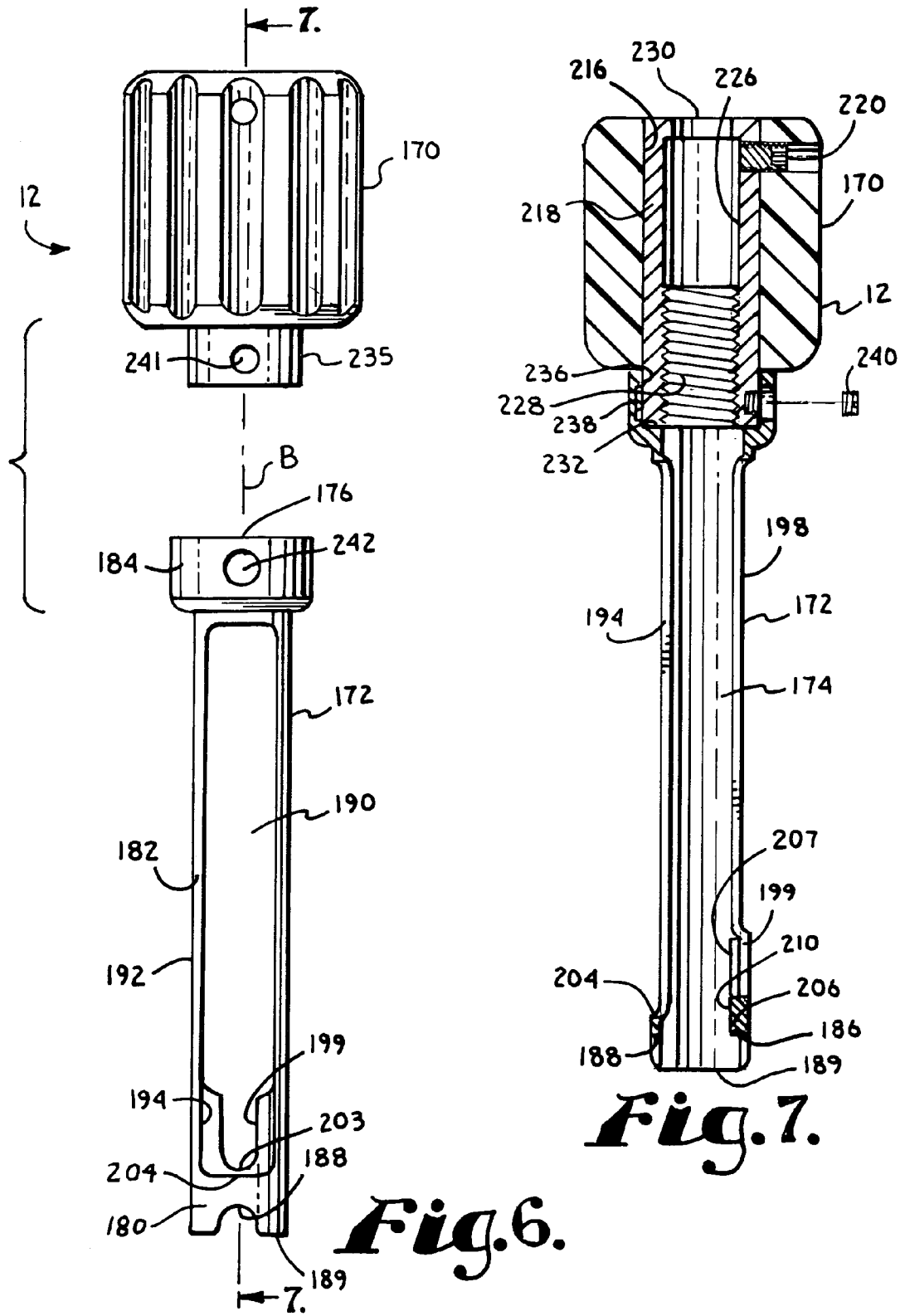

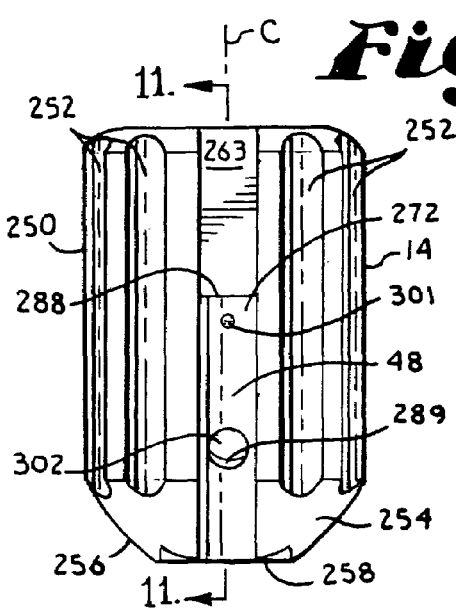
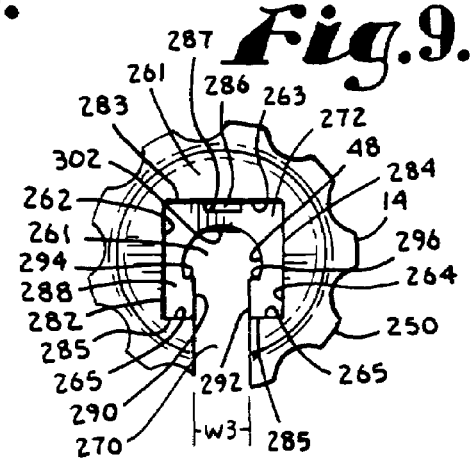
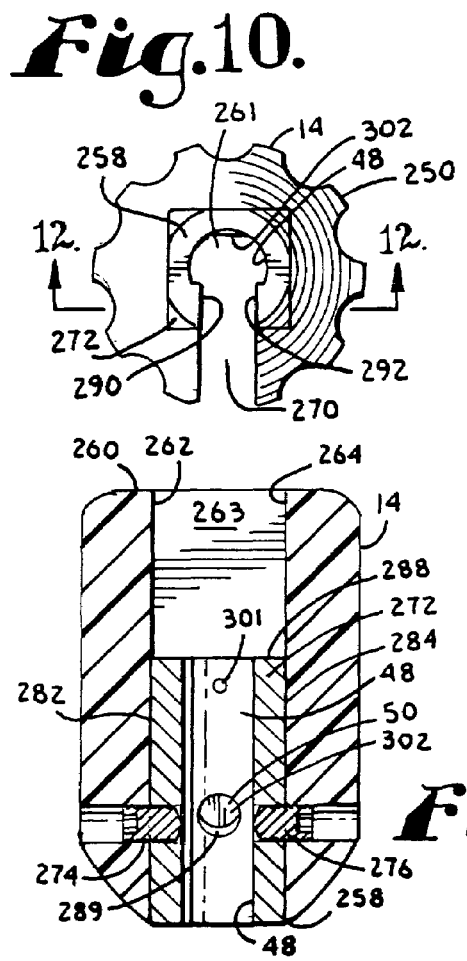
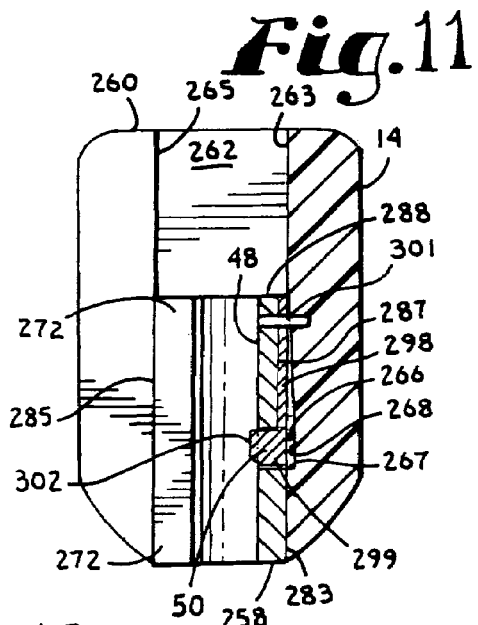

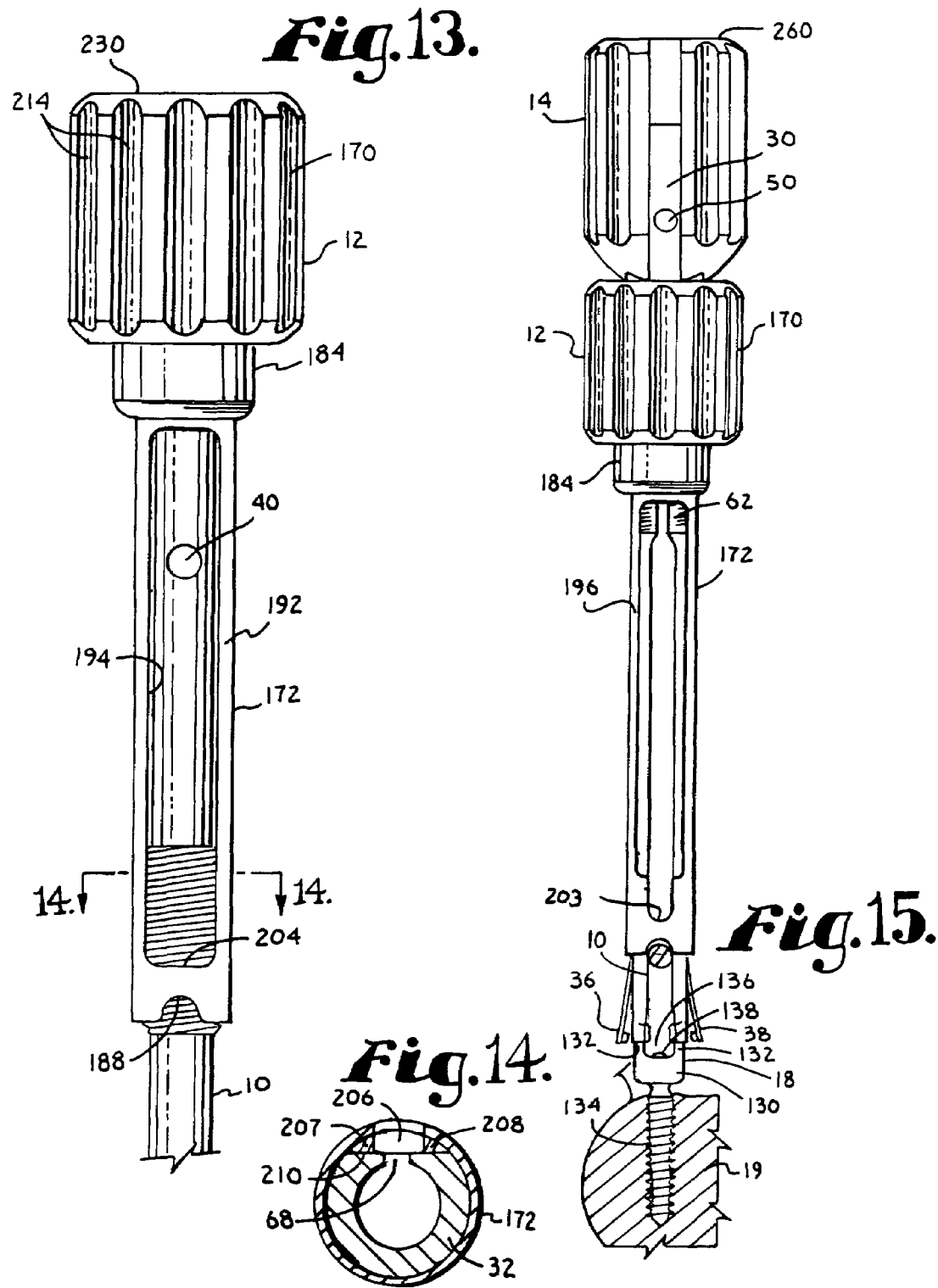

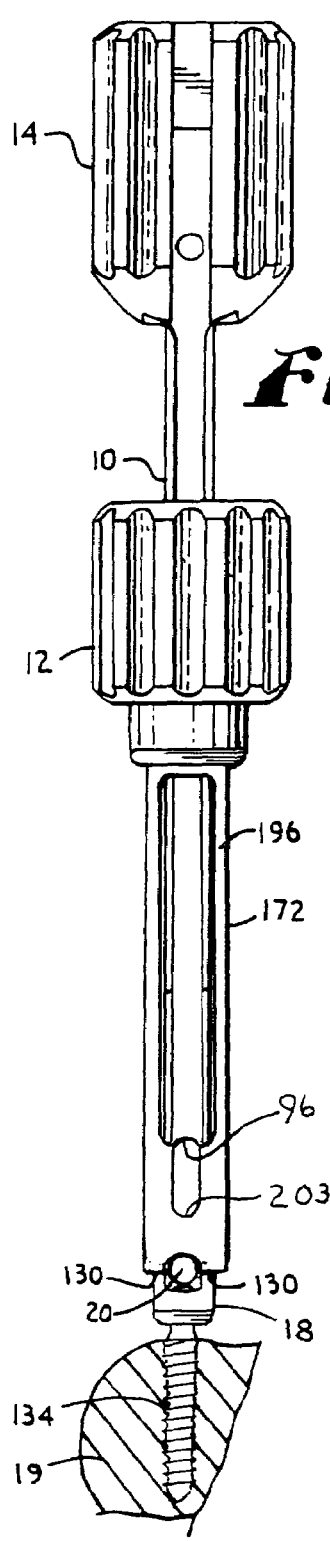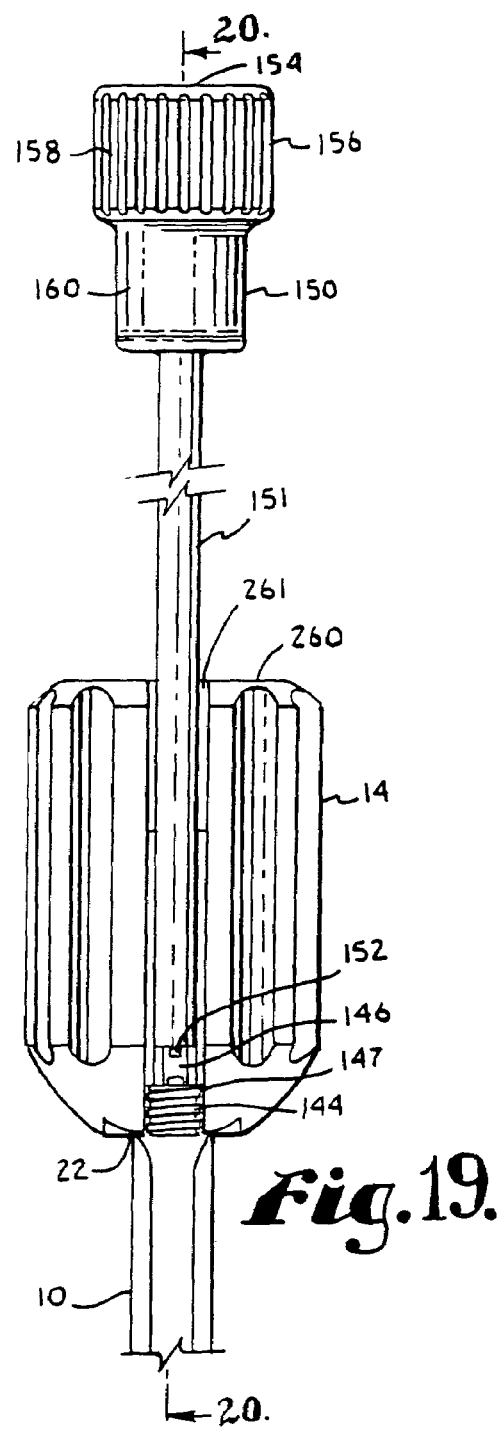
Fig. 18.
Fig. 19.

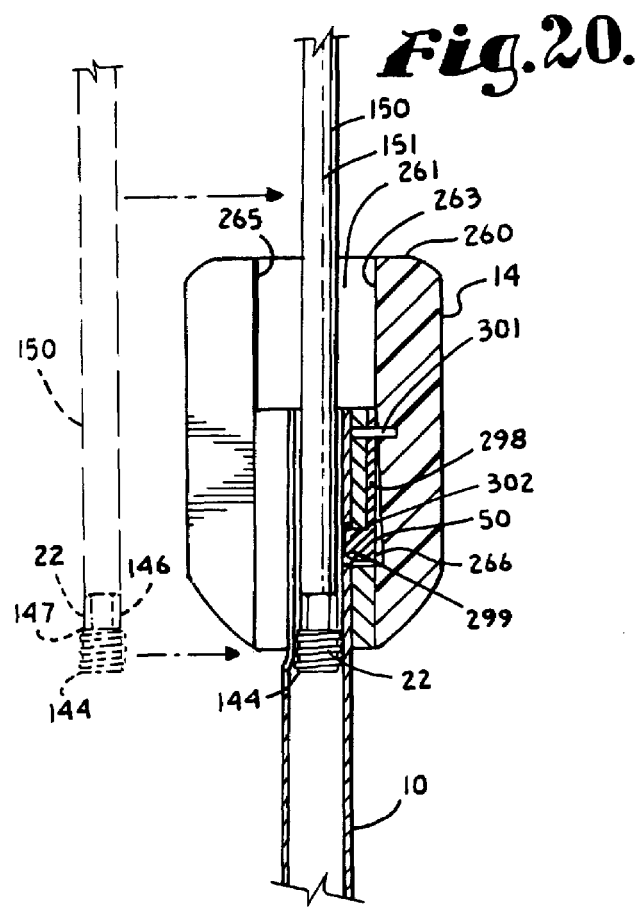
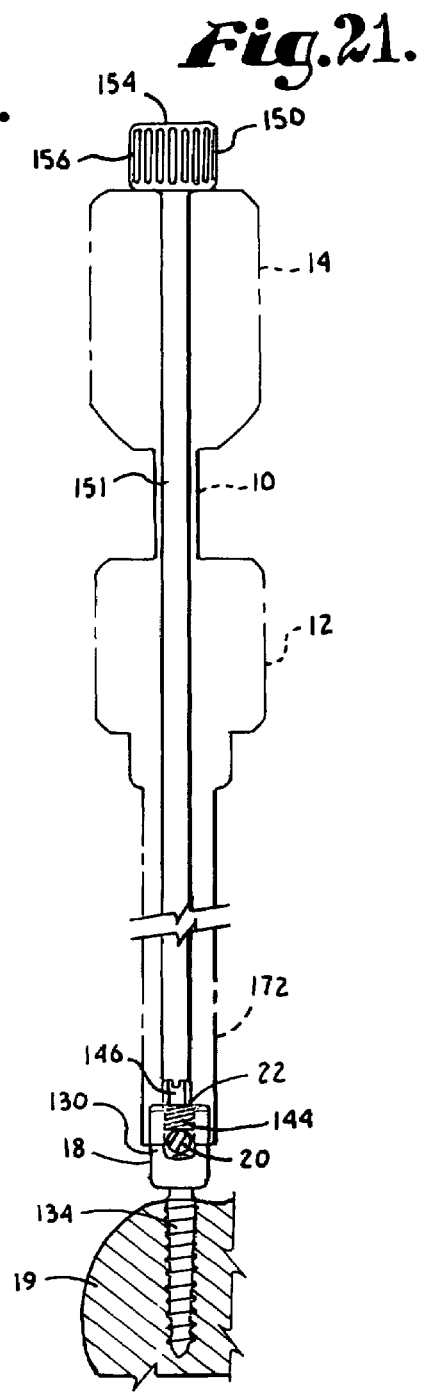

SPINAL FIXATION TOOL SET AND METHOD FOR ROD REDUCTION AND FASTENER INSERTION

BACKGROUND OF THE INVENTION

The present invention relates to apparatuses and methods for use in performing spinal surgery and, in particular, to tools and methods of using such tools, especially for implanting a rod for spinal support and alignment.

For many years, spinal osteosynthesis apparatuses have been utilized to correct spinal deformities, injuries or disease. In such procedures, elongate rods are surgically attached to vertebrae of the spine to provide support and/or to realign or reposition certain vertebrae. Such rods are secured to vertebrae utilizing bone screws and other spinal implants. In particular, bone screws with open ended heads are often utilized for such surgery, with the rod being placed into an open end of one or more implants and then the open end or ends being closed or capped to secure the rod to the implant.

Rods utilized in spinal surgery are often bent or formed to support the spine in a desired manner, or to exert a desired corrective or stabilizing force on the spine. Thus, to obtain such a desired alignment, rods must often be forced into open ended spinal implants.

In order to reduce the impact of such surgery on the patient, a desirable approach is to utilize implanting tools and procedures that have a low profile, resulting in less trauma to the body of the patient. Problems arise when implantation tools designed for traditional surgery that is highly invasive are utilized. The tools may be bulky, oversized or have irregular surfaces or protrusions. A projecting actuator arm or fastening member may provide adequate mechanical advantage to force a rod into a head of an implant, but there may be insufficient clearance to use such structure and/or such structure may produce additional trauma or damage to the patient.

Consequently, it is desirable to develop apparatuses and techniques that allow for the securing of a rod to a bone screw or other implant already attached to a vertebra with significantly less invasion into the body of the patient. At the same time, it is desirable to develop such apparatuses and techniques that provide adequate mechanical advantage to force the rod into position within the bone screw and thereafter hold the rod in place during closing or capping of the bone screw head.

SUMMARY OF THE INVENTION

A guide tool structure or assembly according to the invention is provided for implanting a spinal rod into bone screws or other spinal implants already implanted in a bone. The tool includes an elongate guide structure having a handle structure at one end thereof and opposed implant engaging structure at another end thereof. The implant engaging end is configured for releaseable attachment to an implanted bone screw or other spinal implant. The guide member body defines a channel having a lateral opening along an entire length thereof. The channel is sized and shaped for side loading and receiving of an implant fastener or closure member at one or more loading locations intermittently positioned along the length of the channel. Preferably, side loading is performed at the handle structure.

An embodiment of a tool assembly according to the invention further includes an elongate installation tool or rod pushing member having a translation nut and an attached sleeve. The translation nut is coaxial with the sleeve and freely rotatable with respect thereto. The nut is configured for rotatable attachment to the guide member. In a particular embodiment according to the invention, the guide member has an outer surface with a first guide and advancement structure thereon, such as a helically wound thread, and the translation nut has an inner surface having a second guide and advancement structure thereon, mateable with the first guide and advancement structure. Thus, rotation of the translation nut when the first and second guide and advancement structures are mated causes non-rotating axial translation of the sleeve along the guide member.

In an embodiment according to the invention, the sleeve includes a rod pushing end that functions both to press or reduce a rod into a spinal implant and also to radially press against the guide member end into engagement with the spinal implant.

The assembly may further include a handle, preferably configured for releaseable attachment to the guide member. In particular, in an embodiment according to the invention, the handle has a spring-loaded pin configured to project into an aperture disposed on an upper portion of the guide member when the handle is received on the guide member. The handle includes a channel configured for coaxial alignment with the guide member channel, and a lateral opening configured for coaxial alignment with the guide member lateral opening. The handle lateral opening is configured for receiving a manipulation tool and other spinal implant components, such as a closure top or other spinal implant members utilized for attaching a rod to the spinal implant.

In a particular embodiment according to the invention, a guide member includes a bone screw attachment end having first and second legs defining first and second lateral openings for receiving a rod therethrough. Furthermore, the first leg defines a first slot and the second leg defines a second slot. First and second opposed spring tabs are attached to the first and second legs, respectively. Each spring tab has a protrusion or projection configured for projecting through one of the slots, and into an aperture of a bone screw or other spinal implant. The first and second spring tabs bias the protrusions away from the first and second slots. When assembled with the installation tool or rod pushing member, the spring tabs are pressed radially inwardly by an inner surface of the rod pushing member, which in turn urges the guide member protrusions into bone screw or other spinal implant apertures.

Thus, the assembly according to the invention may be described as having two different configurations. In a first implant receiving configuration, the installation tool is received on the guide member, the nut rotatably attached to the guide member, the handle received on the guide member with the spring-loaded pin disposed in the aperture and the handle in contact with the translation nut. In such configuration, the spring tabs are biased radially outwardly to an extent that the protrusions or projections are not projecting completely through the slots defined by the legs.

In a second, spinal implant holding and rod reducing position, the translation nut is spaced from the handle, and the sleeve of the installation tool is pressing against the spring tabs, urging the protrusions or projections into and through the slots of the guide tool, and if properly aligned with a spinal implant, projecting the protrusions into the spinal implant apertures, thus attaching the guide member to the implanted bone screw or spinal implant.

The rod pushing member sleeve may then be translated downwardly toward the implant, by rotating the translation nut, the rod pushing end pressing a rod downwardly into the implant and holding the rod within the implant during attachment of a closure top or other closure structure onto the spinal implant utilizing the laterally opening channel in the handle for the insertion of closure structure components down the guide member channel and onto the spinal implant. Furthermore, after a rod is attached to the spinal implant, the guide member and attached rod pushing member are easily and readily removed from the implant by simple translation of the rod pushing member sleeve up and off outer surfaces of the spring tabs.

OBJECTS AND ADVANTAGES OF THE INVENTION

Therefore, the objects of the present invention are: to provide a low profile, compact tool assembly for supporting bone screws and installing other implants with minimal trauma to the patient; to provide a tool assembly for implanting a spinal rod for support or alignment along a human spine with minimal trauma to the patient; to provide such a tool assembly including a guide member for slidably guiding a rod toward a bone screw attached to the guide member; to provide such a tool assembly including rod and implant fastener installation tools for assisting in securing the rod in the bone screws; to provide such a tool assembly wherein the guide member is easily and readily attached to and disengaged from bone screws; to provide such a tool assembly wherein the guide member, rod reduction tool, and closure top installation tools are all easily aligned, positioned, and engaged, if necessary, with respect to the bone screw and are disengaged from the bone screw and other tools in the installation assembly by manual manipulation of the surgeon; to provide a method of implanting a rod into bone screws within a patient with minimal surgical trauma to the patient; and to provide such a tool assembly and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is a partial rear elevational view of the guide member of FIG. 1.

FIG. 3 is a partial side elevational view of the guide member of FIG. 2.

FIG. 4 is a partial front elevational view of the guide member of FIG. 2.

FIG. 5 is a cross-sectional view, taken along the line 5-5 of FIG. 2.

FIG. 6 is an exploded rear elevational view of the rod pushing member of FIG. 1.

FIG. 7 is a cross-sectional view of the rod pushing member, taken along the line 7-7 of FIG. 6.

FIG. 8 is the front elevational view of the handle shown in FIG. 1.

FIG. 9 is a top plan view of the handle of FIG. 8.

FIG. 10 is a bottom plan view of the handle of FIG. 8.

FIG. 11 is a cross-sectional view of the handle taken along the line 11-11 of FIG. 8.

FIG. 12 is a cross-sectional view of the handle taken along the line 12-12 of FIG. 10.

FIG. 13 is a partial rear elevational view of the guide member and rod pushing member of FIG. 1 shown at an early stage of installation.

FIG. 14 is a cross-sectional view, taken along the line 14-14 of FIG. 13.

FIG. 15 is a reduced front elevational view of an assembled guide member, rod pushing member and handle of FIG. 1, further shown mounted onto a bone screw implanted in a vertebra, with the rod pushing member in an implant receiving position.

FIG. 16 is an enlarged perspective view similar to FIG. 15, with portions broken away to show the detail thereof.

FIG. 17 is an enlarged cross-sectional view, taken along the line 17-17 of FIG. 16.

FIG. 18 is a reduced front elevational view of the assembled guide member, rod pushing member, handle and bone screw of FIG. 15, shown fully installed in a vertebra, with a rod.

FIG. 19 is an enlarged and partial front elevational view of the handle and assembled guide member of FIG. 17 shown with a closure top manipulation tool and a closure top.

FIG. 20 is an enlarged and partial cross-sectional view of the handle and guide member taken along the line 20-20 of FIG. 19 shown with a closure top manipulation tool and a closure top and further illustrating a side-loading procedure for inserting the closure top manipulation tool and closure top into the handle and guide member assembly (shown in phantom).

FIG. 21 is a reduced and partially schematic view of the assembly of FIG. 18, shown with a closure top installed on the bone screw, the bone screw implanted in a vertebra.

DETAILED DESCRIPTION OF THE INVENTION

Figure 1:
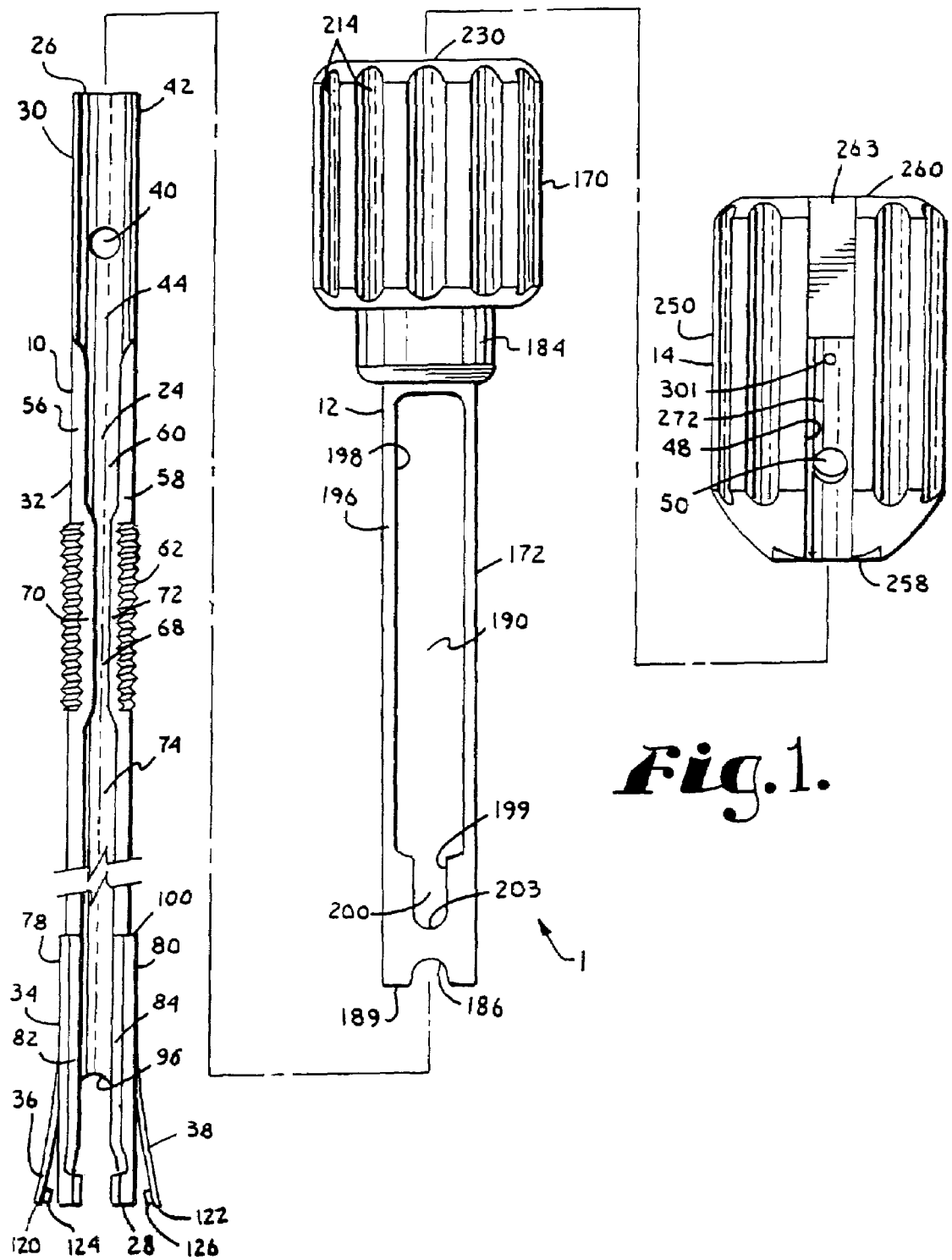
FIG. 1 is an exploded and partial front elevational view of a tool assembly according to the present invention showing an elongate guide member, a rod pushing member, and a handle.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

With reference to FIG. 1, reference numeral 1 generally designates a tool assembly according to the present invention, including a guide structure or member 10 configured for releaseable attachment to a bone screw, attachable to a rod pushing member 12 configured to function as an installation tool that not only pushes or reduces a rod into a bone screw but also presses the guide member into contact and attachment with the bone screw. Also attachable to the guide member 10 is a handle or holder 14 configured to also function as a side-loading manipulation tool guide and support.

The assembly 1 is configured for use with a spinal implant, such as a bone screw 18 that has previously been implanted in a vertebra 19 and a rod 20, also previously inserted in the vicinity of the bone screw 18. The assembly 1 is utilized for reducing the rod 20 or other elongate member into a head of the bone screw 18, and for installing a fastener, such as a closure top 22 or other closure structure to the bone screw 18, capturing the rod 20 within the bone screw 18. The assembly 1 is a particularly helpful tool when the rod 20 is bent relative to the location of the vertebra 19 (which is sometimes the case) to which the rod 20 is to attach and is not easily placed in a head of the bone screw 18 without force. The assembly 1 provides mechanical advantage in such situations. Although not shown, a plurality of assemblies 1 according to the invention may be used as a set for spinal implant procedures so that one guide member 10 is used for each implanted bone screw 18 to which a rod 20 is to be attached. Rods 20 or other longitudinal members are often installed on both sides of the spine during the same procedure.

The elongate guide member 10 is best illustrated in FIGS. 1-5. The elongate guide member 10 is somewhat cylindrical in outer profile. With respect to inner profile, the guide member 10 forms a channel 24 with elongate lateral openings of various widths, configured to receive, contain and allow translational movement along the channel 24, or rotational relative movement of certain tools, as described more fully below. The channel 24 extends from a top 26 to a bottom 28 of the member 10, parallel to a central axis of rotation A thereof. The channel 24 is sized to accommodate elongate tools and bone screw components, such as the fastener or closure structure 22. The guide member 10 is sized and shaped to be sufficiently long to extend from an implanted bone screw 18 through an exterior of a patient's skin, so as to provide an outwardly extending upper or handle portion 30 for attachment to the handle 14, and also for gripping by a surgeon during procedures utilizing the guide member 10, with or without an attached installation tool or rod pushing member 12 and/or handle 14. The guide member 10 further includes an intermediate portion 32 equipped for attachment to the rod pushing member or installation tool 12, and a lower bone screw or other implant engaging portion 34 having opposed implant engaging members, such as the opposed, flexible, implant engaging spring tabs or prongs 36 and 38, for securing a bone screw 18 or other implant there between. It is noted that any reference to the words top, bottom, upper and lower, and the like, in this application refers to the alignment shown in the various drawing figures, as well as the normal connotations applied to such devices, and is not intended to restrict positioning of the assembly 1 in actual use.

The guide member 10 upper or handle portion 30 is substantially in the form of a half-cylinder, having a C- or U-shape, end- or cross-section as viewed from the top 26. Disposed centrally in the handle portion 30 is a round aperture 40 that extends from an outer surface or back wall 42 to an inner surface or inner wall 44. The handle portion 30 cooperates with a C-shaped surface formation 48 of the handle 14, illustrated in FIGS. 8 and 9 and discussed more fully hereafter. The aperture 40 is configured and positioned to cooperate with a spring-attachment mechanism 50 disposed on the handle 14, also described more fully hereafter. At the handle portion 30, the inner wall 44 defines the channel 24 and has an elongate, substantially uniform opening 52, opening at the top 26 and having a side-to-side width W, slightly smaller than, or approximately equal to, a diameter of the handle portion 30.

At the intermediate portion 32, a curved, substantially semi-cylindrical back wall 54 is integral to and extends from the handle portion 30. The intermediate portion 32 also includes curved side walls 56 and 58, integral to the back wall 54, the side walls 56 and 58 forming an elongate, substantially uniform channel opening 60 with a side-to-side width W' that is smaller than the width W of the opening 52 at the handle portion 30. The width W of the upper portion 30 is sized and shaped to receive tools and implants, such as the closure structure 22, while the width W' of the intermediate portion 32 is narrower than a width or diameter of the closure structure 22, allowing for the retention of the closure structure 22 within the guide member 10.

Centrally located on the intermediate portion 32 is an outer, helically wound, discontinuous, guide and advancement structure 62 disposed on outer surfaces of the curved back wall 54 and both of the curved side walls 56 and 58. The guide and advancement structure 62 illustrated in the drawing figures is a conventional helically wound V-type thread. However, it is foreseen that buttress threads, helically wound square threads, or other guide and advancement structures may be utilized to cooperate with equivalent or mateable structure within the rod pushing member 12, described more fully below.

The guide and advancement structure 62 extends from an upper location 64 to a lower location 66. Between the upper location 64 and the lower location 66, a channel opening 68 communicating with the channel opening 60, narrows to a substantially uniform side-to-side width W". Thus, the channel 24 has the most narrow width W" along a length L of the guide and advancement structure 62. To form the narrow width W", the side walls 56 and 58 extend to include integral wall extensions 70 and 72, respectively, also along the length L. The wall extensions 70 and 72 are substantially co-planar and have a smooth, flat surface. The flat wall extensions 70 and 72 aid in providing a guide for orienting and installing the rod pushing member 12 with respect to the guide member 10 as will be described more fully below. Between the guide and advancement structure 62 and the lower portion 34, the walls 56 and 58 form a channel opening 74 that has the same side-to-side width W' as the channel opening 60.

The lower implant engaging portion 34 has a channel opening 76 with the same side-to-side width W' as the channel openings 60 and 74. All of the channel openings, 52, 60, 68, 74 and 76 communicate to provide a lateral opening disposed along an entire length of the guide member 10. The channel opening 76 is sized and shaped to slidingly receive a rod 20 therein. It is foreseen that the channel opening 68 may include width variations to allow for side loading of a fastener into the channel 24.

Also at the lower portion 26, the substantially cylindrical side walls 56 and 58 extend to the bottom 28 of the guide member 10 and further include integral, outer side walls 78 and 80, respectively. The walls 78 and 80 uniformly increase the thickness of the respective side walls 56 and 58. The walls 78 and 80 are configured with co-planar, flat and smooth front surfaces or facets 82 and 84, respectively, that are also coplanar with the wall extensions 70 and 72, providing for alignment and mating with an interior of the rod pushing member 12 to ensure that the guide member 10 is retained in a selected, non-rotatable position with respect to the rod pushing member 12 when installed therein.

The cylindrical back wall 54 also extends into the lower portion 34 of the guide member 10. Integral thereto is a curved back wall support 86 having a radially extending thickness approximately equal to the radial thickness of the walls 78 and 80, similarly uniformly increasing the thickness of the back wall 54. Formed in the back wall support 86 is a slot or channel opening 88, disposed between and defined by first and second back legs, 90 and 92. The slot 88 is disposed opposite the channel opening 76, and an upper portion thereof has a substantially uniform side-to-side width equal to the width W' of the channel opening 76, for receiving a rod 20 therethrough. An upper, curved rod abutment arch or surface 96, defines an upper end of the slot 88, the arch 96 for contacting the rod 20 as the guide member 10 is inserted on the bone screw 18 as will be described more fully subsequently herein. It is foreseen that the back wall 54 and the back wall support 86 may include a narrow slot or slit extending upwardly axially from the arch 96 for providing increased flexibility when inserting the guide member 10 on a bone screw 18 or other implant. Such a slit would render the outwardly biasing spring tabs 36 and 38 unnecessary, allowing for opposed implant engaging members on the guide member 10 to spring apart and thus be snapped or twisted on and off a bone screw or other implant. It is also foreseen that in other embodiments according to the invention, the location of the arch 96 may be moved axially upward, to near the intermediate portion 32 of the guide member 10, providing an elongate through-slot to allow for use of the assembly 1, for example, in a percutaneous procedure wherein the rod 20 is laterally inserted and received in such slot after the member 10 is attached to the bone screw 18.

Disposed between the back wall support 86 and the walls 78 and 80 are the spring tabs 36 and 38, respectively. The tabs 36 and 38 are elongate and fixed to the lower portion 34 with screws 98 disposed near a ledge 100 formed by substantially flush upper end surfaces of the walls 78 and 80, the back wall support 86, and the spring tabs 36 and 38. With the exception of the facets 82 and 84, near the ledge 100, the side walls 78 and 80, the back wall support 86, and the spring tabs 36 and 38 cooperate to form a substantially cylindrical outer surface having an outer diameter greater than an outer diameter of the intermediate portion 32.

Also near the ledge 100, the side walls 56 and 58 and the back wall 54 form an integral, curved, inner surface 101, sized and shaped to accept a closure structure 22 therethrough, but sized smaller than a width or diameter of a head of a bone screw 18. At the rod abutment arch 96, the inner surface 101 divides into two inner surfaces or legs 102 and 103, separated by the slot 88. Near the bottom 28 of the guide member 10, the inner surfaces 102 and 103 are recessed, with a discontinuous bone screw abutment surface or stop 106 partially defining the recess. The abutment surface 106 is substantially annular and disposed perpendicular to the axis A. Inner surfaces 108 and 110 disposed adjacent and substantially perpendicular to the abutment surface 106 also define the recess and are configured to extend about arms of a head of a bone screw 18, substantially following the curvature thereof, slidingly mating therewith along the axis A. Furthermore, the inner surfaces 108 and 110 are configured to align a rod receiving channel in the bone screw 18 with the channel opening 76 and the slot 88 and prohibiting rotational movement of the bone screw 18 about the axis A when the screw 18 abuts the surface 106. Located at the bottom 28 and extending centrally through each of the surfaces 108 and 110 are u-shaped apertures or slots 112 configured to expose apertures 114 in the bone screw 18 to the spring tabs 36 and 38 when the guide member 10 is disposed about the bone screw 18 with the bone screw 18 abutting the abutment surface 106. The slots 112 are disposed in diametrically opposed relation when viewed in cross-section.

With reference to FIG. 3, both of the spring tabs 36 and 38 extend from the ledge 100 to distal ends 120 and 122 that are disposed slightly below the bottom 28 of the guide member 10. Disposed on an inner surface of each spring tab 36 and 38, near respective distal ends 120 and 122, are diametrically opposed implant engaging protrusions or pins 124 and 126, respectively. The tabs 36 and 38 bias outwardly away from the axis A, such that, when the guide member 10 is not installed in the rod pushing member 12, the tabs 36 and 38 splay radially outwardly from the guide member 10 with the protrusions 124 and 126 disposed outside of a periphery of the side walls 78 and 80. However, compression of the tabs 36 and 38 toward the axis A causes the protrusions 124 and 126 to be received in the slots 112. As will be discussed more fully below, when the guide member 10 is slidably received on a bone screw 18, and the rod pushing member or installation tool 12 is mounted on the guide member 10, the protrusions 124 and 126 align with apertures 114 on the bone screw 18 and extend through the slots 112 and into the apertures 114, fixing the bone screw 18 to the guide member 10 when the rod pushing member 12 substantially contacts and compresses the spring tabs 36 and 38. It is noted that other orientations and sizes of protrusions 124 and 126, or other opposed implant engaging structure may be utilized according to the invention, with such structure cooperating with respective features on the guide member 10 and bone screw 18. It is further foreseen that the guide member 10 may be configured for receiving the bone screw 18 from a side thereof, for example, the slot 88 may be of increased width to allow for lateral insertion of the guide member 10 onto the bone screw 18.

The guide member 10 cooperates and mates with a head 130 of the bone screw 18 at upper arms 132 thereof. The apertures 114 identified above are rounded diametrically opposed formations, centrally located in each of the arms 132. With reference to FIGS. 14, 15 and 19, each of the bone screws 18 further includes a threaded shank 134 attached to the head 130, the shank 134 for screwing into and seating in a vertebra 19 that is part of the human spine. The arms 132 of the head 130 define a rod receiving channel 136 passing therethrough. The bone screw shank 134 includes an upper portion 138 that extends into the head 130 and is operationally secured therein, so that the head 130 is rotatable on the shank 134 until locked in position through engagement with the rod 20 under pressure. For example, the shank 134 may be connected to the head utilizing a spline capture connection as disclosed in U.S. Pat. No. 6,716,214 from U.S. Ser. No. 10/464,633, which is incorporated by reference herein.

The closure structure, top or fastener 22 closes between the spaced bone screw arms 132 to secure the rod 20 in the channel 136. The closure top 22 can be any of many different plug type closures. With reference to FIGS. 19-20, preferably the closure top 22 has a cylindrical body with a helically wound mating guide and advancement structure 144. The guide and advancement structure 144 can be of any type, including V-type threads, buttress threads, reverse angle threads, or square threads. Preferably the guide and advancement structure 144 is a helically wound flange form that interlocks with a reciprocal flange form as part of a guide and advancement structure on an interior of the bone screw arms 132. A suitable locking guide and advancement structure of this type is disclosed in U.S. Pat. No. 6,726,689 from U.S. Ser. No. 10/236,123 which is incorporated herein by reference.

Each closure structure 22 also preferably includes a break-off head 146 that breaks from the threaded cylindrical body 144 in a break-off region 147 upon the application of a preselected torque, such as 95 to 120 inch-pounds. The break-off head 146 preferably has a hexagonal cross section faceted exterior that is configured to mate with a similarly shaped socket of a final closure driving or torquing tool (not shown).

Also preferably, the break-off head 145 has an inner cylindrical surface and a pass-through slot configured to cooperate with an elongate manipulation tool 150. The tool 150 has an elongate body 151 configured and sized for insertion into the guide member 10 and handle 14, with a break-off head engaging end that includes a projection receivable into the inner cylindrical surface of the break-off head 145 and a pair of diametrically opposed pins 152 receivable in the head 145 pass through slot. The break-off engaging end may include a slot or other feature to provide for sufficient frictional engagement between the tool 150 and the closure structure 22 so that the closure structure 22 does not slip off the tool 150 as the structure 22 is placed into the handle 14 and the guide member 10 as will be described more fully below. It is foreseen that different configurations of manipulation tool engaging ends may be utilized, depending upon the geometry of the closure structure 22.

At an opposite end or top 154, the manipulation tool 150 has a handle 156 that is substantially cylindrical in shape and is shown with an end portion having outer grooves 158 to aid a surgeon in axially handling and controlling the tool 150 and rotating the closure structure 22. The handle 156 further includes a lower portion 160 that is also substantially cylindrical, but smooth and having a smaller diameter than a diameter of the end grooved portion 158. The lower portion 160 is integral to or otherwise attached to both the end grooved portion 158 and the elongate body 151.

The present invention is not intended to be restricted to a particular type of bone screw or bone screw closure mechanism. In the present embodiment, a polyaxial type bone screw 18 is utilized wherein the shank 134 is locked in position by direct contact with the rod 20. It is foreseen that the tool assembly 1 of the present invention can be used with virtually any type of bone screw, including fixed monoaxial and polyaxial bone screws of many different types wherein the head is locked relative to the shank by structure other than in the manner described in the illustrated embodiment.

With reference to FIGS. 1 and 6-7, the installation tool or rod pushing member 12 of the tool assembly 1 of the invention preferably includes an upper translation nut 170 rotatably and free wheelingably attached to a lower guide member retaining and rod pushing sleeve 172. The sleeve 172 has an inner substantially cylindrical surface 174 defining a substantially hollow passageway 176 sized and shaped to slidingly receive the guide member 10 therein. Alternatively, is foreseen that the sleeve could have an inner and outer planar surface. The sleeve 172 is elongate and includes a receiving end portion 180, a substantially cylindrical outer body 182 and a translation nut attachment end portion 184 disposed opposite the receiving end portion 180. Near the receiving end portion 180, the sleeve inner surface 174 is configured for contacting the spring tabs 36 and 38 of the guide member 10 and pressing the tabs 36, 38 through the slots 112 and into the apertures 114 of a bone screw 18.

The receiving end portion 180 not only functions to receive the guide member 10 into the sleeve 172, but also includes a pair of diametrically opposed U-shaped arches 186 and 188, both adjacent a bottom 189 of the sleeve 172. The arches 186 and 188 are sized and configured for curving about a rod 20, and for pressing the rod downwardly into a bone screw 18 while restricting any lateral movement of the rod 20 during translation of the rod 20 toward the bone screw head 130 by rotation of the translation nut 170, when the rod pushing member 12 is installed on the guide member 10, as will be discussed more fully below.

The sleeve 172 further defines an elongate squared-off through-slot or opening 190. With reference to FIG. 6, at a rear side 192 of the sleeve 172, the slot 190 is defined by a substantially rectangular border or perimeter 194. The rear side 192 also defines the arch 188. With reference to FIG. 1, at a front side 196, the pass-through slot 190 is defined in part by a substantially rectangular border or perimeter 198 that is diametrically opposed and a mirror image of the border 194, with the exception of a lower substantially U-shaped border 199, defining a U-shaped opening or slot 200. The substantially U-shaped border 199 on the front side 196 does not have a similar or mirror-image component on the rear side 192. The slot 200 defined by the U-shaped border 199 has a side-to-side width approximately equal to the width W' of the channel openings 60, 74 and 76 of the guide member 10. The U-shaped slot 200 is centrally located on the front side 196 of the sleeve 172 and is defined in part by a base portion 203 that is spaced from the arch 186. The base portion 203 is substantially diametrically opposed to a base 204 of the substantially rectangular border 194, the base 204 spaced from the arch 188 a distance slightly less than a distance separating the base portion 203 from the arch 186.

With reference to FIG. 14, the inner surface 174 of the cylindrical portion 202, has a plate 206 fixed thereto disposed between the base 203 of the U-shaped slot 200 and the arch 186. The plate 206 also includes plate extensions 207 and 208, extending upwardly on either side of the slot 200. The plate 206 and extensions 207 and 208 are coplanar, forming a smooth, flat inner surface 210 substantially parallel to an axis B of the rod pushing member 12. The plate 206 and extensions 207 and 208 are integral or otherwise fixed, such as by welding, to the inner cylindrical surface 174. The planar surface 210 provides structure for installing the guide member 10 in a mating and desired alignment with respect to the rod pushing member 12 with the surface 210 slidably contacting the co-planar surfaces 70 and 72 during insertion of the guide member 10 into the rod pushing member 12. Thereafter, the co-planar facets 82 and 84 contact the surface 210, with the surface 210 preventing axial rotation of the member 10 with respect to the sleeve 172, resulting in a preferred alignment of the arches 186 and 188 with the lower channel opening 74 and the slot 88. The plate 206 extends to the arch 186, providing added thickness, and thus mechanical advantage where the arch 186 contacts with a rod 20 when the rod pushing member 12 pushes the rod 20 toward a bone screw 18.

The translation nut 170 of the rod pushing member 12 is substantially cylindrical in shape and is shown with outer grooves 214 to aid a surgeon in handling the rod pusher 12 and rotating the nut 170. With reference to FIG. 7, the nut 170 further includes an inner cylindrical surface 216 for fixed attachment to a substantially cylindrical insert 218 utilizing screws or pins 220. The cylindrical insert 218 also defines an inner substantially cylindrical passage 226 communicating with the passage 176 of the sleeve 172. The inner surface 216 further includes a helical guide and advancement structure as shown by a V-shaped thread 228 that is configured to mate with the guide and advancement structure 62 of the guide member 10.

Also with reference to FIG. 7, the inner cylindrical surface 216 extends from an upper open end 230 of the translation nut 170 to an inner annular seating surface 232 of the sleeve 172, the surface 232 extending radially outwardly and perpendicular to the cylindrical surface 216. The guide and advancement structure 228 terminates at the seating surface 232. As will be discussed more fully below, the surface 216 with associated thread 228 is of a length that provides an equivalent translation distance of the rod pushing member 12 with respect to the guide member 10 such that the arches 186 and 188 can be used to gradually push the rod 20 toward the bone screw 18 for the entire translation distance by rotating the nut 170 until the rod 20 is fully seated in the head of the bone screw. It is foreseen that other structure may be utilized to provide for translation of the sleeve 172 along the guide member 10, such as a frictional or ratchet structure.

Further with reference to FIG. 7, at the annular seating surface 232, the sleeve 172 is in sliding, rotational contact with the nut 170 about the axis B. The insert 218 includes a lower portion 235 extending below the translation nut 170 and disposed opposite the upper open end 230. The translation nut attachment portion 184 of the sleeve 172 defines an inner cylindrical surface 236 of slightly greater diameter than an outer diameter of the insert portion 235. The surface 236 is configured to slidingly receive the nut lower portion 235 along the surface 236. The sleeve 172 further defines an annular recess or groove 238 configured to receive a screw 240 rigidly fixed to the insert lower portion 235 at an aperture 241. The screw 240 may be accessed for attachment and removal from the lower portion 235 through an aperture 242 disposed in the sleeve translation nut attachment portion 184. The screw 240 slidingly mates with the sleeve portion 184 that defines the recess 238, keeping the nut 170 and sleeve 172 in an attached, but freely rotatable relation.

With reference to FIGS. 8-12, the handle 14 of an assembly 1 according to the invention is preferably detachable and includes an outer, substantially cylindrical surface 250 shown with grooves 252 to aid a surgeon in handling the assembly 1 for assembly of the handle 14 with the guide member 10, insertion of the guide member 10 on a bone screw 18 and for stationary gripping and stability during rotation of the rod pusher translation nut 170. The cylindrical surface 250 is disposed substantially parallel to an axis C of the handle 14. At a lower portion 254 of the handle 14, an outer, substantially conical surface 256 extends from the cylindrical surface 250 toward the axis C, to a substantially flat lower end or bottom surface 258, disposed perpendicular to the axis C. The handle 14 also includes a substantially flat top surface 260 parallel to the bottom surface 258.

The handle 14 further defines an elongate through-bore 261 extending centrally along the axis C from the top surface 260 to the bottom surface 258, the bore 261 being defined in part by substantially planar, rectangular, inner surfaces 262, 263, 264 and 265. With the exception of a portion of the surface 263, each of the surfaces 262, 263, 264 and 265 are disposed substantially parallel to the axis C and form substantially square end- and cross-sections as illustrated in FIGS. 9 and 10. However, the surface 263 also forms a recess 266 defined by a flat, rectangular surface portion 267 disposed substantially perpendicular to the axis C and a flat, rectangular surface portion 268 disposed at an angle slightly less than 90 degrees with respect to the surface portion 267, the surface portion 268 extending between the surface portion 267 and a portion of the surface 263 disposed substantially parallel to the axis C. The recess 266 receives the spring attachment 50 as discussed more fully below.

The surface 265 is discontinuous, broken by an elongate slot 270 formed in the handle 14, extending from the top surface 260 to the bottom surface 258, the slot 270 communicating with the bore 261 along an entire length thereof. The slot 270 opens laterally to the surface 250 and has a side-to-side width W3 that is larger than the width W'. The width W3 is also slightly larger than a diameter of the threaded cylindrical body 144 of the closure structure 22. The slot 270 is configured to laterally receive the manipulation tool 150 and an attached closure structure 22 or other fastener, and allow radial movement thereof toward the axis C until the tool 150 is disposed centrally in the bore 261. Thereafter, the bore 261 accommodates translational movement therealong and rotational movement of the tool 150, as described more fully below. It is foreseen that according to the invention, the rod pushing member 12, at both the nut 170 and sleeve 172, may also include a slot with a lateral opening of a width and orientation to operably communicate with the slot 270 of the handle 14 and the channel 24 of the guide member 10.

An insert 272 is disposed within the bore 261 and fixedly attached to the handle 14 at the planar inner surface 262 by a pin 274 and at the planar inner surface 264 by a pin 276. Outer, substantially planar and rectangular surfaces 282, 283, 284 and 285 are contiguous to and contact the inner surfaces 262, 263, 264 and 265 respectively, with the pin 274 extending through the surface 282 and the pin 276 extending through the surface 284. Similar to the surface 265, the surface 285 is discontinuous and broken by the elongate slot 270. The surface 283 includes an upper elongate recess 286 disposed centrally therein and defined in part by a planar surface 287 disposed spaced from and parallel to the surface 283. The recess 286 communicates fully with the slanted recess 266 formed in the inner surface 263. The surface 287 originates at a top planar surface 288 of the insert 272 and terminates at a rounded aperture 289 formed in the insert 272. The aperture 289 is spaced from the bottom 258 of the handle 14 and extends radially from the surface 283 and the surface 287 to the C-shaped inner surface 48. The recess 286 and the aperture 289 are configured for receiving the spring attachment 50, described more fully below.

The insert 272 extends from the bottom surface 258 to the top planar surface 288. The top planar surface 288 is disposed within the bore 261, spaced from the top 260, and is oriented substantially parallel to the top 260 and perpendicular to the axis C. The C-shaped surface 48 partially defines an inner portion of the insert 272 and partially defines the through-bore 261. Parallel walls 290 and 292 partially define the slot 270 and co-planar connecting walls 294 and 296 are disposed between the C-shaped surface 48 and respective walls 290 and 292. The co-planar walls 294 and 296 provide abutment surfaces for the alignment and attachment of the upper portion 30 of the guide member 10 with respect to the handle 14.

The spring attachment 50 is substantially L-shaped in cross-section as shown in FIG. 11, having an upper leg 298 and a lower leg or protrusion 299 integral and substantially perpendicular to the upper leg 298. The upper leg 298 is fixed between the handle inner surface 263 and the insert surface 287 by a pin 301 disposed near the insert top surface 288. The upper leg 298 has a thickness slightly less than a distance between the surface 283 and the surface 287 at the recess 286. Thus, near the insert top surface 288, the upper leg 298 preferably contacts both the insert surface 287 and the inner surface 263, with the surface 263 and the pin 301 urging the upper leg 298 in contact with the surface 287 along a length thereof. The lower leg or protrusion 299 is configured to extend through the aperture 298, having an end portion 302 extending beyond the C-shaped surface 48 and into the bore 261. The end portion 302 is configured to be received by the aperture 40 of the guide member 10. When a radial outward force is placed on the end portion 302, the protrusion 299 is urged into the aperture 298 and the upper leg 298 extends into the recess 266 formed in the handle surface 263. Such a radial force is placed on the end portion 302 when a guide member 10 is received into the bore 261 as will be described more fully below.

With reference to FIGS. 1 and 13-18, a three-component assembly 1 according to the invention including the guide member 10, rod pushing member 12 and the handle 14 is assembled as follows: The guide member 10 is inserted into the rod pushing member 12 with the upper end 26 being inserted into the receiving end or bottom 189 of the rod pushing member 12. The guide member 10 is received into the rod pushing member 12 with the channel opening 52 facing the arch 186 and the U-shaped slot 200, and the outer surface or back wall 42 facing the arch 188 and the substantially rectangular border 194 as shown in FIG. 13. As the guide member 10 is received into the rod pushing member 12, rotational movement is prevented by the flat surface 210 of the plate 206 and plate extensions 207 and 208, in sliding contact with the flat wall extensions 70 and 72 of the guide member 10. The translation nut 170 is then rotated clock-wise as viewed from the upper end 230, with the thread 62 of the guide member 10 mating with the thread 228 disposed on the inner surface of the translation nut 170. The translation nut 170 is then rotated until the entire upper or handle portion 30 of the guide member 10 is positioned outside of the upper end 230 of the nut 170, and to where the side walls 56 and 58 begin, with a small section of the thread 62 exposed by the slot 190 as shown in FIG. 15.

During rotation of the translation nut 170, the guide member 10 is held in position and any rotational movement of the member 10 is prevented by the alignment plate 206 and extensions 207 and 208 in contact with the co-planar walls or facets 82 and 84 of the guide member 10.

With reference to FIG. 15, after installation of the rod pushing member 12 to the guide member 10, the handle 14 is inserted into the guide member 10 exposed upper or handle portion 30 by inserting the portion 30 into the bore 261 at the bottom 258 of the handle 14 with the outer back wall 42 in contact with the C-shaped surface 48 and the channel opening 52 facing the slot 270. The handle portion 30 is slid axially along the C-shaped surface and into the bore 261 with the back wall 42 forcing the spring attachment end portion 302 into the aperture 289, thereby forcing the spring attachment 50 into the recess 266, until the aperture 40 of the guide member 10 is aligned with the aperture 289. Upon such alignment, the spring attachment 50 biases the end portion 302 back through the aperture 289 and also through the guide member aperture 40, fixing the handle 14 to the guide member 10. During assembly of the handle 14 onto the guide member 10, the axial and radial alignment of the aperture 40 with respect to the aperture 289 is provided by the abutment walls 294 and 296 disposed at either side of the C-shaped surface 48, contacting edges of the guide member portion 30 that define the channel opening 52, and thus prohibiting rotational movement of the handle 14 with respect to the guide member 10.

With reference to FIGS. 15-17, the axes A, B, and C of the assembly 1 are now aligned and the assembly 1 is in a bone screw or other implant engaging configuration, with the channel 24 aligned with the bore 261. In such configuration, the rod pushing member sleeve 172 is disposed about the guide member lower portion 235, but at a distance from the bottom 28 of the guide member 10 such that the sleeve 172 does not bias the spring tab protrusions 125 and 126 completely through the slots 112. However, in the implant engaging position, the sleeve 172 is preferably placing some pressure on the spring tabs or prongs 36 and 38, with the respective protrusions 124 and 126 disposed partially within the slots 112 as shown in FIG. 17 in readiness for bone screw attachment.

In use, the assembly 1 is utilized to attach one or more rods 8 to the human spinal column 6. The procedure is begun by selection of a bone screw 18 in accordance with the size of the patient's vertebra 19 and the requirements of the spinal support needed. Bone screws 18 having a rotatable or polyaxial head 130 are preferred but not required for the procedure, as such allow relatively easy adjustment of a rod 20. Preferably the assembly 1 is utilized in a traditional, open procedure, wherein a long incision is made along the spinal column to accommodate the length of the rod, the bone screws 18 are then implanted, followed by the rod 20. After placement of the rod along the length of the incision to a location near the bone screws 18, the assembly 1 is inserted over the rod 20 and onto a bone screw 18. However, it is foreseen that in certain minimally invasive or percutaneous procedures, the guide member 10 may be attached to the bone screw 18, followed by lateral insertion of the rod 20 through the slot or lateral opening 88 of the member 10.

The bone screws 18 are typically implanted into a bone, such as the vertebra 19, by rotation of the shank 134 using a suitable driving tool (not shown) that operably drives and rotates the shank 134 by engagement thereof with apertures or other tool engagement apparatus located at or near the upper portion of the shank 138. It is foreseen that before the bone screw 18 is implanted in the vertebra 19 it may be desirable to attach an elongate guide tool (not shown) to the bone screw head 130, utilizing the apertures 114. Such a guide tool (not shown) is of a length similar to the guide member 10 so as to aid a surgeon in holding and placement of the bone screw 18, and also provide stability during the bone screw driving process.

After the rod 20 is inserted near the implanted bone screw or screws 18, an assembly 1 according to the invention is preferably attached to the bone screw 18 to provide mechanical advantage for pushing the rod 20 into the bone screw head 130. The assembly 1 of the invention is typically attached to the bone screw 18 after the rod 20 is positioned in the vicinity of the bone screw head or heads 130, as close as possible to respective rod receiving channels 136. The assembly 1, configured in the implant engaging position shown in FIG. 15 is then guided downwardly through an incision (not shown) to straddle the rod 20 within the slot or channel opening 88 of the guide member 10 and between the back legs 90 and 92 and the front facets 82 and 84. The assembly 1 is then joined to a bone screw 18 by inserting the lower implant engaging portion 34 about the bone screw head 130, aligning the slot 88 with the bone screw rod receiving channel 136, with the guide member lower portion 34 and associated spring tabs 36 and 38 aligned with the upper arms 132 as shown in FIGS. 15-17. The assembly 1 is then slid along the bone screw head 130 until the head 130 contacts the abutment surface 106. Any rotational movement between the assembly 1 and the head 130 is prohibited by the inner sleeve surface 174 that is configured to follow the curvature of the head upper arms 132 and partially wrap about edges of the arms 132. The translation nut 170 is then rotated in a clock-wise direction, as viewed from the handle 14, lowering the sleeve 172 along the spring tabs 36 and 38 and biasing the tabs radially inwardly, with the protrusions 124 and 126 projecting through the U-shaped slots 112 and into the bone screw apertures 114, thereby fixing the bone screw 18 to the assembly 1. The surgeon turns the translation nut 170 with one hand while holding the assembly 1 at the handle 14 with the other hand, providing support and stability during attachment of the assembly 1 to the bone screw 18. When the rear arch 188 of the rod pushing member 12 is co-aligned and substantially flush with the rod abutment arch 96 of the guide member 10, the protrusions 124 and 126 are seated fully within the bone screw apertures 114. An advantage of the assembly 1 according to the invention is that no twisting or other rotational or lateral movement occurs during attachment of the assembly 1 to the bone screw 18 that may cause trauma to human tissue. All twisting and rotation movement is performed outside the skin at the translation nut 170.

As already mentioned herein, it is foreseen that in certain minimally invasive procedures, it may be desirable to first insert the assembly 1, or possibly just the guide member 10, onto an implanted bone screw 18 and thereafter slide the rod 20 through the slot 88, capturing the rod 20 between the bone screw head 130 and the rod abutment arch 96 and/or arches 186 and 188 of the rod pusher 12.

After the assembly 1 is attached to the bone screw 18, the rod 20 is pushed downwardly into the rod receiving channel 136 and then into abutment with the upper shank portion 138, by rotating the translation nut 170 in a clockwise direction (as viewed from above the handle 14), thereby translating the sleeve 172 in a downward direction toward the bone screw 18, with the plate 206 abutting and pushing against the rod 20. The translation nut 170 is rotated clockwise until the rod 20 is seated against the upper shank portion 138 as shown in FIG. 18.

As shown in FIG. 19-21, after the rod 20 is positioned within the bone screw 18, a fastener or closure structure 22 is transported down the channel 24 utilizing the manipulation tool 150. It is foreseen that it may also be desirable to additionally push the rod 20 toward the screw 18, simultaneously with the rod reduction performed by rotating the translation nut 170. As shown in FIGS. 19 and 20, the closure structure 22 attached to the manipulation tool 150 is placed in the elongate top to bottom channel 24 of the guide member 10, preferably by entry from the side through the slot 270 of the handle 14 that communicates fully with the channel 24 at the upper handle portion 30 of the guide member 10. The manipulation tool 150 is moved laterally through the slot 270 until both the closure structure 22 and the tool 150 are disposed centrally in the channel 24, which is also centrally located in the bore 261 of the handle 14. The manipulation tool 150 is then moved downwardly through the channel 24 toward the bone screw 18. Alternatively the closure structure 22 that has been attached to the manipulation tool 150 may be inserted into the bore 261 at the top 260 of the handle 14 and then moved down the channel 24. As the closure structure 22 and tool 150 pass through the intermediate portion 32 of the guide member 10, the side walls 56 and 58 prohibit passage of the closure structure 22 out of the channel 24 and further provide axial alignment of the elongate body 151 of the tool 150.

Once the closure structure 22 abuts against the upper arms 132 of the bone screw 18, the manipulation tool 150 is rotated in a clockwise direction, mating a helically wound guide and advancement structure disposed on inner surfaces of the bone screw arms 132 with the threaded cylindrical body 144 of the closure structure 22, so as to drive the closure structure 22 downward against the rod 20 and to further urge the rod 20 downward into the bone screw channel 136. With reference to FIG. 21, continued rotation of the tool 150, utilizing the handle 156, drives the rod 20 downward and into engagement with the upper portion of the bone screw shank 138, so as to snug against and frictionally lock the shank 134 in position relative to the bone screw head 130.

Once all of the closure structures 22 or other fasteners utilized in a particular procedure are in final seated position in respective bone screws 18 and the surgeon is satisfied with the position of all of the elements, the manipulation tool 150 is removed by pulling upwardly and sliding the tool 150 out of the assembly 1 through the channel 24. The assembly 1 is then removed from the bone screw 18 by rotating the translation nut 170 counter-clockwise until the translation nut top 230 abuts the handle bottom 258. As the sleeve 172 moves upward and off of the spring tabs 36 and 38, the protrusions 124 and 126 spring out of the apertures 114, freeing the assembly 1 from the bone screw 18. Then, the assembly 1 is pulled upwardly, out of the incision.

If desired, a torquing tool (not shown) is then inserted into the incision and utilized to engage with the break-off head 146 and apply a preselected torque, which breaks the head 146 from the closure top 22, and is thereafter removed.

It is to be understood that while certain forms of the present invention have been illustrated and described herein, it is not to be limited to the specific forms or arrangement of parts described and shown.

What is claimed and desired to be secured by Letters Patent is as follows:

1. A spinal rod implantation tool assembly comprising:
   a) a guide member having an elongate body, a bone screw attachment end, and an outer surface having a first guide and advancement structure thereon, the body defining an elongate channel, the body further defining a first elongate lateral opening communicating with the channel, the bone screw attachment end having
      i) first and second legs defining in part the first lateral opening and defining a second lateral opening opposed to the first lateral opening, the first leg defining a first slot and the second leg defining a second slot; and
      ii) first and second opposed spring tabs, the first tab attached to the first leg and the second tab attached to the second leg, each spring tab having a protrusion configured for projecting through one of the slots, and into an aperture of a spinal implant, the first and second spring tabs biasing the protrusions away from the first and second slots;
   b) an elongate installation tool having a translation nut and an attached sleeve, the translation nut coaxial and being freely rotatable with respect to the sleeve, the nut having an inner surface with a second guide and advancement structure thereon, mateable with the first guide and advancement structure, the sleeve having a rod pushing end, the rod pushing end configured for pressing radially inwardly against the spring tabs and thereby projecting the protrusions through the slots and into apertures of a spinal implant, the rod pressing end also configured for contact with and translation of a rod toward the spinal implant; and
   c) a handle configured for releaseable attachment to the guide member, the handle having a second channel configured for coaxial alignment with the first channel, and a second lateral opening configured for coaxial alignment with the first lateral opening, the second lateral opening configured for receiving a manipulation tool.

2. The assembly of claim 1 further comprising a manipulation tool having a holder and a stem, the stem having an end configured for rotatable engagement with a closure member of a spinal implant, the stem configured to be in coaxial relationship with both the first and second channels, the stem insertable into the handle second channel through the second lateral opening.

3. A spinal rod implantation tool assembly comprising:
   a) an elongate guide member having an end configured for releaseable attachment to a spinal implant and a first channel having a first lateral opening along an entire length of the guide member;
   b) an elongate installation tool having a translation nut and an attached sleeve, the translation nut coaxial and being freely rotatable with respect to the sleeve, the nut configured for rotatable attachment to the guide member, the sleeve having a rod pushing end, the rod pushing end translatable along the guide member and configured for pressing the guide member end into engagement with the spinal implant and for contact with and translation of a rod toward the spinal implant;
   c) a handle configured for releaseable attachment to the guide member, the handle having a second channel configured for coaxial alignment with the first channel, and a second lateral opening configured for coaxial alignment with the first lateral opening; and
   d) a manipulation tool having a holder and a stem, the stem having an end configured for rotatable engagement with a closure member of a spinal implant, the second lateral opening configured to receive the manipulation tool; the stem configured to be in coaxial relationship with both the first and second channels, the stem laterally insertable into the handle second channel.

4. The assembly of claim 3 wherein:

a) the guide member has an outer surface having a first guide and advancement structure thereon; and b) the translation nut has an inner surface having a second guide and advancement structure thereon, mateable with the first guide and advancement structure, and wherein rotation of the translation nut when the first and second guide and advancement structures are mated causes non-rotating axial translation of the sleeve along the guide member.

5. A spinal rod implantation tool assembly comprising:

a) an elongate guide member having an end configured for releaseable attachment to a spinal implant and a first channel having a first lateral opening along an entire length of the guide member;

b) an elongate installation tool having a translation nut and an attached sleeve, the translation nut coaxial and being freely rotatable with respect to the sleeve, the nut configured for rotatable attachment to the guide member, the sleeve having a rod pushing end, the rod pushing end translatable along the guide member and configured for pressing the guide member end into engagement with the spinal implant and for contact with and translation of a rod toward the spinal implant; and c) the guide member end having first and second opposed spring tabs disposed on either side of the first lateral opening, each spring tab having a protrusion configured for attachment to a spinal implant, the spring tabs biasing radially outwardly and away from the guide member end, the installation tool sleeve configured for pressing the spring tabs inwardly radially and toward the spinal implant; and d) a handle configured for releaseable attachment to the guide member, the handle having a second channel configured for coaxial alignment with the first channel, and a second lateral opening configured for coaxial alignment with the first lateral opening, the second lateral opening configured for receiving a manipulation tool.

6. A spinal rod implantation tool assembly comprising:

a) an elongate guide member having an end configured for releaseable attachment to a spinal implant and a first channel having a first lateral opening along an entire length of the guide member; the guide member having an aperture;

b) an elongate installation tool having a translation nut and an attached sleeve, the translation nut coaxial and being freely rotatable with respect to the sleeve, the nut configured for rotatable attachment to the guide member, the sleeve having a rod pushing end, the rod pushing end translatable along the guide member and configured for pressing the guide member end into engagement with the spinal implant and for contact with and translation of a rod toward the spinal implant; and c) a handle configured for releaseable attachment to the guide member, the handle having a second channel configured for coaxial alignment with the first channel, and a second lateral opening configured for coaxial alignment with the first lateral opening, the second lateral opening configured for receiving a manipulation tool; the handle has a spring-loaded pin configured to project into the guide member aperture when the handle is received on the guide member with the first and second channels in coaxial alignment.

7. The assembly of claim 6 having a first implant receiving configuration and a second implant holding and rod reducing configuration, the first configuration wherein the installation tool is received on the guide member, the nut rotatably attached to the guide member, the handle received on the guide member with the spring-loaded pin disposed in the aperture and the handle in contact with the translation nut, the second position wherein the translation nut is spaced from the handle, with the sleeve pressing the guide tool into engagement with the spinal implant.

8. The assembly of claim 7 wherein the guide member end has first and second opposed spring tabs disposed on either side of the first lateral opening, each spring tab having a protrusion configured for attachment to a spinal implant, the spring tabs biasing radially outwardly and away from the guide member end, the installation tool sleeve pressing against the spring tabs and urging the protrusions inwardly radially toward the spinal implant when the assembly is in the second implant holding and rod reducing configuration.

* * * * *

UNITED STATES PATENT AND TRADEMARK OFFICE
CERTIFICATE OF CORRECTION

PATENT NO. : 7,651,502 B2
APPLICATION NO. : 10/950377
DATED : January 26, 2010
INVENTOR(S) : Roger P. Jackson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1425 days.

Signed and Sealed this

Twenty-third Day of November, 2010

David J. Kappos
*Director of the United States Patent and Trademark Office*